United States Patent [19]

Carlson

[11] Patent Number: Plant 7,527

[45] Date of Patent: May 21, 1991

[54] NECTARINE TREE CARLSON VARIETY

[76] Inventor: H. David Carlson, P.O. Box 9304, Yakima, Wash. 98909

[21] Appl. No.: 462,139

[22] Filed: Jan. 8, 1990

[51] Int. Cl.[5] ..... A01H 5/00
[52] U.S. Cl. ..... Plt./41
[58] Field of Search ..... Plt./41

*Primary Examiner*—James R. Feyrer

*Attorney, Agent, or Firm*—Chernoff, Vilhauer, McClung & Stenzel

[57] ABSTRACT

A nectarine tree which is of medium size and vigor, spreading, vase formed; foliated with medium size reniform glands; blooms medium season from medium size buds which are plump, appressed, pubescent and pink in color; and is a regular and productive bearer of medium size, symmetrical, uniform, globose, semi-freestone fruit having orange-yellow skin substantially overspread with red when the fruit is fully ripe.

1 Drawing Sheet

BACKGROUND AND SUMMARY OF THE INVENTION

This new variety of nectarine tree was discovered as a whole tree chance seedling in a block of RedGold nectarines by Mr. H. David Carlson of Yakima, Wash. in the year 1983. The RedGold nectarine block which had been planted in 1978 is located in the Parker Heights district of the Lower Yakima Valley near Parker, Wash. At the time of discovery the four (4) year old seedling was producing its second crop of fruit.

Asexual reproduction of the new variety was successfully accomplished in the year 1984 by budding to peach seedling stocks. The second generation asexually reproduced trees, upon maturity, have run true to the original seedling tree in all respects.

This present new variety of nectarine tree is of medium size and vigor, spreading and vase shaped. It is foliated with medium size, ovate, lanceolate, acutely pointed leaves having a crevate margin and reniform glands. The pink flowers are medium season from medium size, plump appressed and pubescent flower buds. It is a regular and productive bearer of medium size, symmetrical, uniform, globose, semi-freestone fruits. The attractive bright red fruits are underlaid with an orange-yellow ground color. The yellow flesh is mottled with red next to the stone which is brown in color.

The present variety of nectarine tree is further characterized by its fruit which ripens fourteen (14) days before the RedGold variety of nectarine thus providing a nectarine harvest and market availability intermediate and seven (7) days after of the popular Firebrite variety (unpatented) in the fruit growing areas of Eastern Washington.

DETAILED DESCRIPTION OF THE INVENTION

Figure 1:
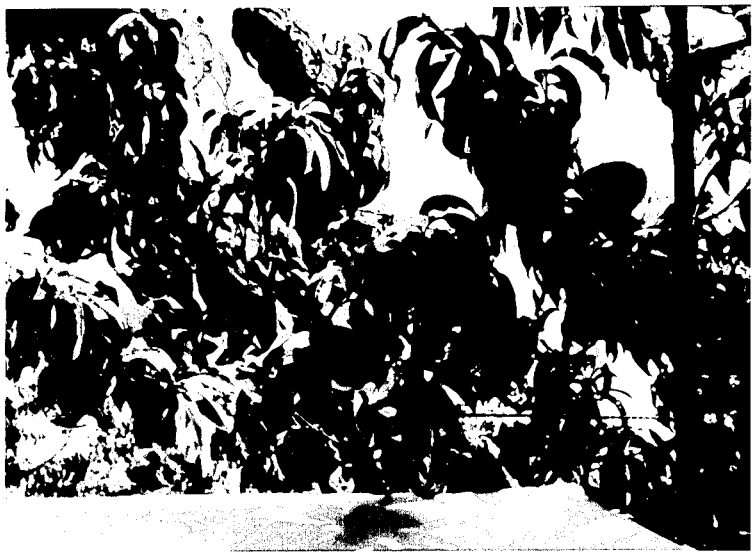
FIG. 1 shows the vegetative growth and fruits of a mature specimen of the subject variety on the tree.
Figure 2:
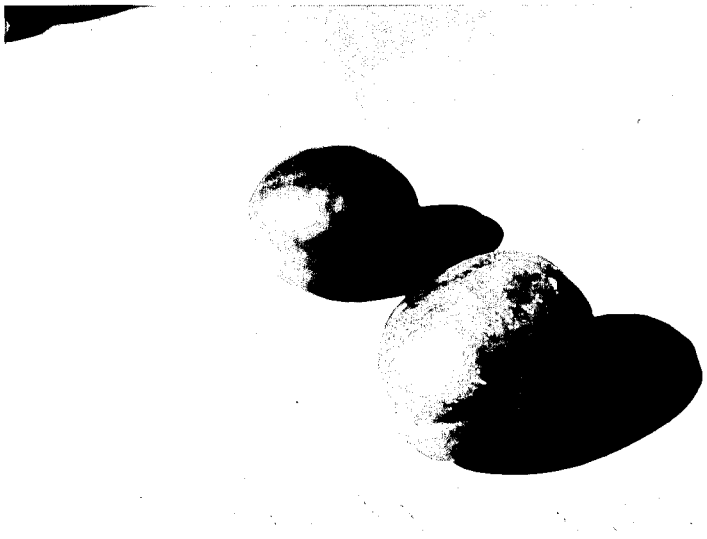
FIG. 2 shows the fruit of the subject variety off of the tree.

The following is a detailed description of the new variety of nectarine tree and its flowers, foliage and fruit based on observations of specimen trees growing at Wapato and Parker, Wash. All major color descriptions being by reference to the *Munsell Color Cascade Chart* except where general color terms of ordinary dictionary significance are used.

Tree:
- *Size.*—Medium.
- *Vigor.*—Medium.
- *Growth.*—Spreading.
- *Density.*—Medium.
- *Form.*—Vase formed.
- *Production.*—Productive.
- *Bearing.*—Regular bearer.

Trunk:
- *Size.*—Medium.
- *Texture.*—Medium.

Branches:
- *Size.*—Medium.
- *Texture.*—Smooth.
- *Color.*—New wood: light green. Reddish brown on ventral side. Mature wood: brown.

Leaves:
- *Size.*—Medium. Average length — 15.8 cm. average width 4.2 cm.
- *Form.*—Lanceolate. Acutely pointed. Ovate.
- *Thickness.*—Medium.
- *Color.*—Medium green (20-21). Underside — lighter green (19-10).
- *Texture.*—Smooth.
- *Margin.*—Crevate.
- *Petiole.*—Medium length — average 1.3 cm. Medium thickness.
- *Glands.*—Medium size, Reniform. Average number — 3. Position alternate usually 3 on petiole and 1-3 on blade.

Flower buds:
- *Size.*—Medium.
- *Length.*—Medium.
- *Form.*—Plump. Appressed. Pubescent.
- *Hardiness.*—Hardy.

Flowers:
- *Date of full bloom.*—April 5.
- *Size.*—Medium.
- *Color.*—Pink (41-5).

Fruit:
- *Maturity when described.*—Firm ripe — August 4.
- *Date of first picking.*—August 1.
- *Date of last picking.*—August 10.

*Size.*—Medium. Average diameter axially 6.4 cm. Average transversely in suture plane — 6.2 cm.
*Form.*—Uniform, Symmetrical globose.
*Suture.*—Distinct.
*Ventral surface.*—Rounded.
*Cavity.*—Rounded. Elongated in suture plane. Average depth — 1.2 cm. Average breadth — 1.8 cm.
*Markings.*—None.
*Base.*—Rounded.
*Apex.*—Short. Depressed.
*Pistil point.*—Apical.

Skin:
*Thickness.*—Medium.
*Texture.*—Medium.
*Color.*—Ground color — orange yellow (32-6). Blush color — Red (36-11).
*Tenacity.*—Tenacious to flesh.
*Tendency to crack.*—None.
*Down.*—Wanting.

Flesh:
*Color.*—Yellow (29-5).
*Juice.*—Abundant.
*Texture.*—Firm, crisp.
*Fibers.*—Few, fine.
*Ripens.*—Evenly.
*Flavor.*—Subacid to mild.
*Aroma.*—Distinct.
*Eating quality.*—Best.

Stone:

*Type.*—Semi-free.
*Fibers.*—Short.
*Size.*—Medium. Average length — 3.4 cm. Average breadth — 2.5 cm. Average thickness — 2.0 cm.
*Form.*—Elliptical.
*Base.*—Straight.
*Apex.*—Rounded.
*Sides.*—Equal.
*Surface.*—Furrowed near ventral edge. Ridged toward apex. Pitted at base.
*Pits.*—Elongated.
*Ventral edge.*—Thick.
*Dorsal edge.*—Shallow.
*Tendency to split.*—None noted.
*Color.*—Tan.

General:
*Use.*—Market.
*Keeping quality.*—Good.
*Shipping quality.*—Good.
*Resistance to weeds and disease.*—Usual.

What is claimed is:

1. A new and distinct variety of nectarine tree, substantially as illustrated and described, characterized by the regular and productive bearing of yellow-fleshed, semi-freestone fruit which ripens intermediate to the RedGold and the Firebrite nectarine varieties; it is further characterized by red color which overspreads the entire fruits at harvest time.

* * * * *